United States Patent
Tiller et al.

(10) Patent No.: US 10,780,205 B2
(45) Date of Patent: Sep. 22, 2020

(54) METHOD FOR OPERATING A SUPPLY DEVICE WHICH SUPPLIES A LIQUID TO A CHANNEL, AND SUPPLY DEVICE, HOLLOW CATHETER, AND CATHETER PUMP

(71) Applicant: ECP ENTWICKLUNGSGESELLSCHAFT MBH, Berlin (DE)

(72) Inventors: Melanie Tiller, Berlin (DE); Sami Er, Berlin (DE); Reiner Liebing, Berlin (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 0 days.

(21) Appl. No.: 16/228,005

(22) Filed: Dec. 20, 2018

(65) Prior Publication Data

US 2019/0192752 A1  Jun. 27, 2019

Related U.S. Application Data (63) Continuation of application No. 15/029,092, filed as application No. PCT/EP2014/071706 on Oct. 9, 2014, now Pat. No. 10,195,323.

(30) Foreign Application Priority Data

Oct. 14, 2013  (EP) .................................... 13188579

(51) Int. Cl.
  *A61N 1/362* (2006.01)
  *A61M 1/10* (2006.01)
  (Continued)

(52) U.S. Cl.
  CPC ........ *A61M 1/1008* (2014.02); *A61M 1/1074* (2014.02); *F04B 43/02* (2013.01);
  (Continued)

(58) Field of Classification Search
  CPC .............. A61M 1/1008; A61M 1/1074; A61M 1/1013; A61M 1/102; A61M 1/1034;
  (Continued)

(56) References Cited

U.S. PATENT DOCUMENTS

| 4,895,557 A | 1/1990 | Moise et al. |
| 5,536,242 A | 7/1996 | Willard et al. |

(Continued)

FOREIGN PATENT DOCUMENTS

| CN | 1330561 A | 1/2002 |
| CN | 201293204 Y | 8/2009 |

(Continued)

OTHER PUBLICATIONS

PCT International Search Report and Written Opinion for International Serial No. PCT/EP2014/071706, dated Dec. 17, 2014 (10 pages) with English translation of the International Search Report (3 pages).

(Continued)

*Primary Examiner* — Mallika D Fairchild
(74) *Attorney, Agent, or Firm* — Botos Churchill IP Law LLP (57) ABSTRACT

The present invention relates to a supply device for a channel (8), in particular within a hollow catheter (1), and to a method for operating a supply device of this type that supplies a channel (8) with a liquid and has two pumps (10, 19) arranged at points of the channel distanced from one another, characterised in that the parameter values of at least one operating parameter of both pumps are coordinated with one another in a controlled manner. As a result of the method, interruption-free and precisely controllable operation is to be ensured with simple structural means, in particular in the case of use of wear-free diaphragm pumps.

14 Claims, 5 Drawing Sheets

(51) Int. Cl.
    *F04B 43/02*     (2006.01)
    *F04B 43/04*     (2006.01)
    *F04B 43/08*     (2006.01)
    *A61M 1/12*     (2006.01)

(52) U.S. Cl.
    CPC .............. *F04B 43/04* (2013.01); *F04B 43/08* (2013.01); *A61M 1/101* (2013.01); *A61M 1/102* (2014.02); *A61M 1/1013* (2014.02); *A61M 1/1034* (2014.02); *A61M 1/1086* (2013.01); *A61M 1/122* (2014.02); *A61M 1/125* (2014.02); *A61M 2205/3334* (2013.01)

(58) Field of Classification Search
    CPC ...... A61M 1/122; A61M 1/125; A61M 1/101; A61M 1/1086; A61M 2205/3334; F04B 43/02; F04B 43/04; F04B 43/08
    See application file for complete search history.

(56) References Cited

U.S. PATENT DOCUMENTS

| | | |
|---|---|---|
| 2005/0028551 A1 | 2/2005 | Noda et al. |
| 2010/0025730 A1 | 2/2010 | Heikman et al. |
| 2011/0088619 A1 | 4/2011 | Duerrstein |
| 2011/0112354 A1 | 5/2011 | Nishimura et al. |
| 2012/0178985 A1 | 7/2012 | Walters et al. |
| 2012/0316799 A1 | 12/2012 | Gagel |
| 2016/0250399 A1 | 9/2016 | Tiller et al. |

FOREIGN PATENT DOCUMENTS

| | | |
|---|---|---|
| CN | 101578073 A | 11/2009 |
| DE | 202805 A1 | 10/1983 |
| DE | 10 2010 022 060 A1 | 12/2011 |
| EP | 0635279 A1 | 1/1995 |
| EP | 2363157 A1 | 9/2011 |
| EP | 2388028 A1 | 11/2011 |
| EP | 2389961 A1 | 11/2011 |
| JP | 2005/169094 A | 6/2005 |
| JP | 2011/167461 A | 9/2011 |
| WO | 01/17581 A2 | 3/2001 |
| WO | 2005/011049 A2 | 2/2005 |
| WO | 2009/027116 A1 | 3/2009 |
| WO | 2009/071069 A1 | 6/2009 |
| WO | 2013/045448 A1 | 4/2013 |

OTHER PUBLICATIONS

PCT International Report on Patentability for International Serial No. PCT/EP2014/071706, dated Mar. 14, 2016 (19 pages).
Office Action issued in Korean Patent Application No. 10-2016-7012259 dated Jun. 24, 2020.

METHOD FOR OPERATING A SUPPLY DEVICE WHICH SUPPLIES A LIQUID TO A CHANNEL, AND SUPPLY DEVICE, HOLLOW CATHETER, AND CATHETER PUMP

RELATED APPLICATIONS

This application is a continuation of U.S. application Ser. No. 15/029,092, filed Apr. 13, 2016 (now allowed), which is a national stage filing under 35 U.S.C. § 371 of International Application No. PCT/EP2014/071706, filed on Oct. 9, 2014 and European Patent Application No. 13188579.0, filed Oct. 14, 2013. The specifications of each of the foregoing applications are hereby incorporated by reference in their entirety.

Method for operating a supply device that supplies a channel with a liquid, and supply device, hollow catheter and catheter pump The invention lies in the field of electrical engineering and mechanics and can be used particularly advantageously in the field of medical engineering.

Specifically, the invention concerns the supply of a channel with a liquid. By way of example, it may be necessary to fill a channel with a liquid in order to cool the walls of the channel or to cool or to lubricate moving parts arranged in the channel and/or to make these parts gas-free. For this purpose, it is known in principle to supply a channel of this type, for example a cannula, with a cooling and/or lubricating liquid. The liquid may be moved into the channel or through the channel in principle by means of a pump.

Here, in particular in the case of medical applications, it is often important on the one hand for there to be no abraded parts produced in the channel to be transported by the liquid in the channel, and on the other hand for the speed at which the liquid is moved through the channel to be as slow as possible, but precisely controlled. In addition, it may also be desired to minimise the liquid loss from the channel.

The prior art, for example DE 20 2005 021 999 U1, discloses a heat exchange system having a pump which transports a heat exchange fluid from and to a catheter. A flow detector in the form of an impeller wheel is described, wherein the rotational speed of the impeller wheel moved by the heat exchange fluid corresponds to the flow rate. The speed of the impeller wheel is measured from outside by a light barrier, which is interrupted each time individual blades of the impeller wheel pass through said barrier.

A diaphragm pump for medical use is known from DD 202 805 A1 which is used to convey insulin in small volumes. There, a pulsating delivery mode is also described.

DE 694 09 587 T2 discloses a method for flushing a catheter having an outward and return channel in order to minimise deposits within the catheter to the greatest possible extent. Inter alia, a pulsating flushing is described there, which can be controlled by solenoid valves.

Against the background of the prior art, the object of the present invention is therefore to create a supply device for supplying the channel with a liquid and a method for operating such a supply device, wherein a solution of simple design is sought which makes it possible in a controlled manner to control the flow of the liquid at a slow flow rate.

The object is achieved in accordance with the invention by a supply device and by a method according to the independent claims. Special embodiments are described in the dependent claims.

The invention accordingly relates to a method for operating a supply device that supplies a channel with a liquid and has a diaphragm pump. The method is characterised in that the diaphragm pump is controlled in respect of the generated pressure and/or the delivery rate.

In accordance with the invention, a supply device for supplying a channel with a liquid having at least one diaphragm pump is also proposed. The device has a control device, which controls the pump in respect of the generated pressure (which in some embodiments may also include a negative pressure or a vacuum) and/or the delivery rate.

The invention additionally relates to a hollow catheter and/or a catheter pump. Here, it is important that both have a supply device according to the invention for flushing a channel of the hollow catheter or of the catheter pump in the manner according to the invention.

One embodiment concerns the fact that the accordingly equipped hollow catheter has a rotatable shaft within the hollow catheter (preferably within the channel).

In accordance with a further embodiment a rotatable shaft is likewise passed through the catheter pump, which preferably contains a hollow catheter according to the invention. Here, it is particularly advantageous when this rotatable shaft is flexible. For the example of a left heart-assist system, which is introduced intraventricularly from the leg artery and is advanced until it reaches the left ventricle of the heart, this means that such a pump contains a rotatable shaft that is driven outside the body and drives a rotor in the heart; this shaft must be flexible enough that it for example can follow the curvature of the aortic arch, yet still can rotate at high speed. The shaft rotatable in the lumen/channel to be flushed should be operable at a high rotational speed, which for example may be above 10,000 revolutions per minute.

The supply device according to the invention here ensures the supply with liquid via the supply device according to the invention, for example in order to ensure an absence of air within the hollow catheter or the catheter pump, but also in order to lubricate the flexible shaft.

The invention also relates to a method for operating a supply device which supplies a channel with a liquid and has two pumps arranged at points of the channel distanced from one another. Here, the parameter values of at least one operating parameter of both pumps are controlled in a manner coordinated with one another.

In principle, it is known and possible to move a liquid through a channel by means of a single pump. Due to the features of the invention, in particular the use of a plurality of pumps, it is possible, however, when operating parameters of the pumps are coordinated with one another, for example to set a common pressure level whilst maintaining an appropriate pressure difference between an infeed region and a discharge region of the channel.

Is also possible to control a flow rate by two coordinated pumps in such a way that on the one hand a certain flow rate through the channel can be set and on the other hand loss rates of the liquid in the inlet and outlet region or in the event of leaks/openings present in the channel can be set, in particular limited, to a certain value.

In order to achieve particularly good adjustability and therefore controllability of the operation of the supply device, diaphragm pumps lend themselves particularly for producing the supply devices. These can be controlled particularly accurately and reproducibly in respect of the flow, i.e. the flow rate.

A particularly efficient control of the supply device is possible when the liquid pressure is advantageously detected at two points in the channel distanced from one another. In particular, the points at which the liquid pressure is detected can be assigned each to one of the pumps respectively, and by means of the pressure detection an optimal ratio of suction pressure and overpressure can be provided by control of the pumps. Such a control is important in particular when the channel is not annularly closed, but has an intake area, in which liquid is fed to the channel from outside from a liquid reservoir, and/or has a discharge channel, through which liquid is removed from the channel into a collection reservoir.

The corresponding pressure sensors can be installed separately in the channel, but may also be integrated one in each of the pumps.

It has proven to be particularly advantageous in the case of the method according to the invention for the coordinated parameter values of the two pumps to be variable over time in accordance with a fixed schema and in particular to be changed periodically over time following a start-up phase. By way of example, the capacity of at least one of the pumps can be slowly increased in the start-up phase. However, a capacity peak (performance peak) may also be sought, such that the liquid initially flows at a high flow rate through the channel, wherein the flow rate reduces again following the starting phase.

Irrespectively of the configuration of the start-up phase, the pressure of at least one of the pumps can be controlled so as to rise and fall periodically, or a periodically rising and falling flow rate can be set accordingly. This is then advantageous in particular when moving parts are provided within the channel, for example a driveable shaft within a cannula, which shaft in turn releases small particles as a result of abrasion. These particles usually are not to be moved further along the channel, however the liquid is to be transported nevertheless. Varying the operating parameters of the pumps allows an efficient flushing of the channel with the liquid, wherein all parts of the channel are reached by the non-stationary flow. Due to the phases of slower flow rate of the liquid, the particles can come to a standstill in the flow, such that the transport of the particles along the channel can be minimised.

Variation of the parameters of the pumps, apart from the variation of the capacity (performance) of each of the individual pumps, may also be, for example, a variation of the capacity (performance) difference or of a pressure difference generated by the pumps. The pressure difference ensures the acceleration of the liquid and thus a periodically fluctuating pressure difference for a correspondingly periodically fluctuating liquid transport.

A liquid will be understood hereinafter to mean a liquid used to flush the shaft. In some exemplary embodiments this is not a liquid to be delivered by the pump, although traces or small quantities of liquid to be delivered by the pump may also enter the channel. In other exemplary embodiments the liquid to be conveyed by the pump can be that used for flushing.

In accordance with a further advantageous embodiment of the invention the coordinated parameter values of the two pumps lie at a ratio to one another that is dependent in a predetermined manner on detected values of the liquid pressure in the channel. In this way, the liquid pressure in the channel or a liquid pressure difference can be controlled periodically.

The delivery capacities of the pumps can be determined on the basis of different measurands. In some exemplary embodiments the measurands or operating parameters for determining the delivery capacity are the stroke frequency of the diaphragm and/or the stroke height of the diaphragm and/or the deflection of the diaphragm. Here, in order to determine the delivery capacity, one of the above measurands or a combination of at least two of the above measurands can be consulted. A further possibility for determining the delivery capacity is in some exemplary embodiments the electrical power consumption of the pump, in particular under consideration of the prevailing liquid pressure.

The coordinated operating parameters of both pumps may therefore be, for example, the respective delivery capacities. A certain difference of the delivery capacities may then also be set between the two pumps, for example. This may then for example cause a certain loss rate to be generated for the liquid transport over the course of the channel.

In accordance with a further embodiment of the invention the coordinated operating parameters of both pumps are the respective values of the liquid pressure generated by the pumps. The liquid pressure can be detected particularly easily and accurately in the channel, such that for example a certain quotient of the pressure values or a certain difference of the pressure values can be set by control of the pumps. The quotient and/or the difference may also be set so as to be periodically variable in order to avoid a stationary flow with deadwater areas.

In accordance with a further advantageous embodiment of the invention the coordinated operating parameters of both pumps are the respective electrical power consumptions of the pumps. For this purpose, each pump may be assigned an electric sensor for detecting the power consumption of the pump, in particular for detecting the current consumption.

Advantageously, the coordinated operating parameters of both pumps may additionally be the respective flow rates of the pumps. The flow rates can be detected separately for example by flowmeter sensors, or also by the recording of the operating parameters of the pumps, for example the power consumption and the prevailing fluid pressure.

In addition, a fixed pressure difference and/or a fixed difference of the flow rate advantageously may be set between the two pumps. Here, the difference of the flow rates of both pumps may in particular be less than 100 millilitres per day, in particular less than 10 millilitres per day, or less than 1 millilitre per day.

Corresponding loss rates are set at the openings of the channel. By way of example, the channel may have a transport channel and a return channel, wherein the transport channel ends for example at a blood pump arranged at the end of a cannula and the return channel starts at the same point. Some of the liquid that makes up the difference of the flow rates may then flow off for example through the blood pump, flush this, and in the implanted state may be discharged into the body of a patient. In a development of the invention a biocompatible, health-compatible liquid, for example a saline solution, is selected as liquid in such an application.

With an advantageous form of operation of the method, the direction of movement of the liquid may additionally be reversed. Such a reversal of the direction of movement of the liquid may be provided periodically or also only on certain occasions. In the event of use to flush a pump catheter, a direction of transport of the liquid from a proximal end of the catheter to a distal end of the catheter and back through a return channel into a collecting container is usually selected.

The invention also relates to a method for operating a supply device and to the design of a supply device for supplying a channel with a liquid, said supply device having at least two pumps, in particular diaphragm pumps, which are arranged at points of the channel distanced from one another, and also having a control device, which controls the pumps individually in respect of the generated pressure and/or the delivery rate.

The control device must be designed in such a way that it allows a coordinated control of the individual pumps. It may be assigned to one of the pumps or may also be formed as a separate central control unit. The control device may also serve to regulate operating parameters of the pumps and is then connected to sensors in order to detect measurement values.

By way of example, each pump may be assigned a liquid pressure sensor. By means of the control device, a certain pressure ratio can then be set between suction pressure and overpressure, or a certain quotient of the pressures generated by the two pumps or a certain pressure difference can be set.

Since the measurands for determining the delivery power of the pumps may be pressure-dependent, the pumps for example may be operated as pressure sensors when their power consumption is detected and fed to the control device. However, the power consumption may also be an indicator for the flow rate attained by means of the respective pump and may be detected as such. For this purpose, the prevailing liquid pressure is usually to be taken into consideration in addition, such that the simultaneous operation of pressure measurement sensors is advantageous with operation of this type.

However, flow rate sensors may be provided, which are each assigned to one of the pumps respectively. A certain ratio of the flow rates in the region of the first and second pump or a predetermined difference can then be set by the control device. Such a difference of the flow rates may be controlled for example so as also to be periodically variable.

The invention will be shown in figures of a drawing and described hereinafter on the basis of exemplary embodiments. In the figures

Figure 1:
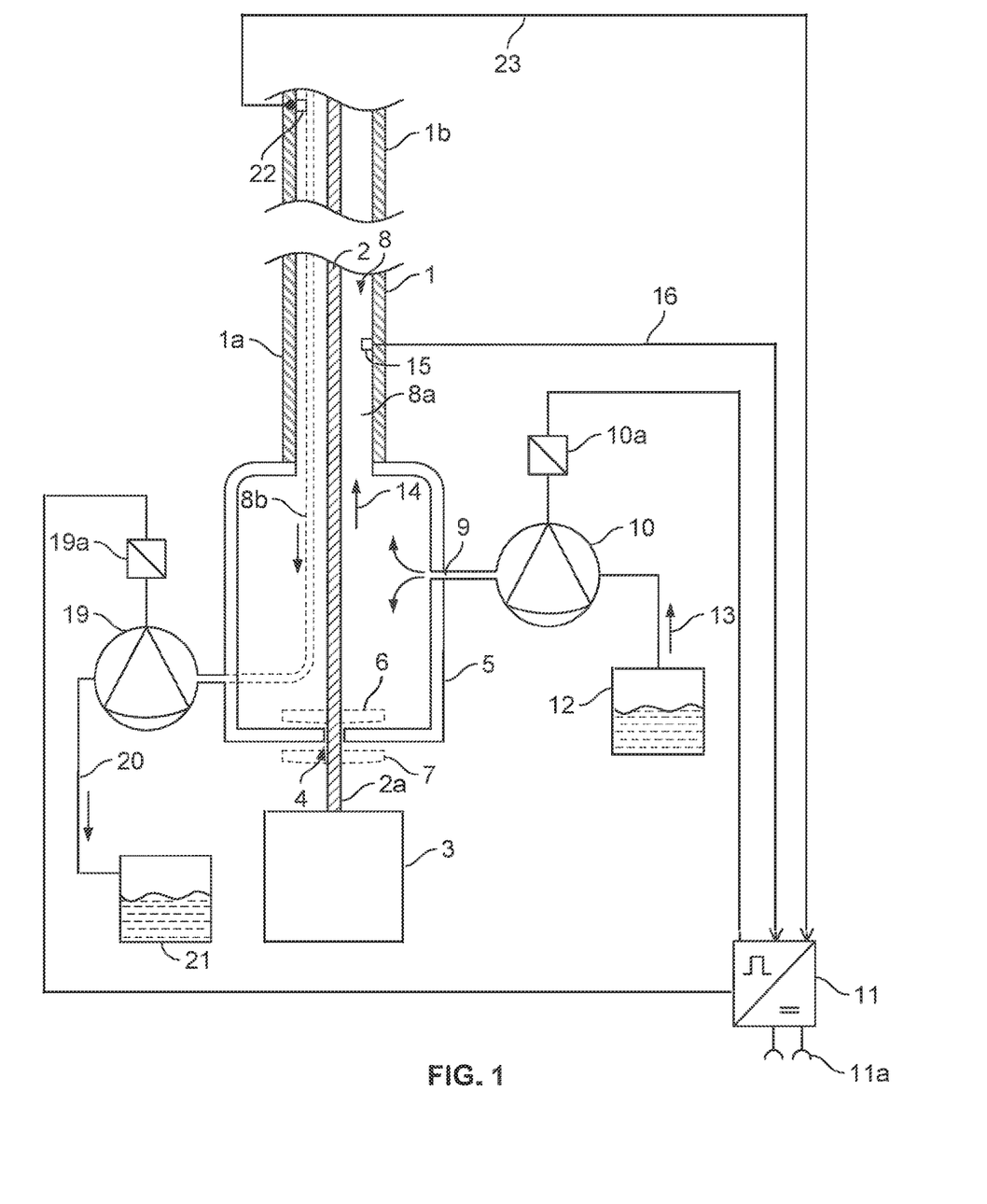
FIG. 1 shows a hollow catheter having a driveable shaft and a supply device according to the invention.

FIG. 1 shows a hollow catheter 1 in an illustration interrupted in the longitudinal direction, wherein an end 1a which is proximal in medical use is illustrated in the lower region and a distal end 1b is illustrated in the upper region. By way of example, an implantable blood pump may be provided at the distal end of the hollow catheter 1, especially for operation in a blood vessel and/or a heart chamber.

A rotatably driveable shaft 2 extends within the hollow catheter 1. This serves for example to drive a blood pump and is connected at its proximal end 2a to a drive motor 3. The shaft 2 can be introduced in the region of a feedthrough 4 into a coupling housing 5, wherein the feedthrough 4 is configured in such a way that a medium is prevented from passing along the shaft into the coupling housing 5 or cut from the coupling housing 5 by a seal.

However, the solution is also conceivable that the rotating drive movement is transmitted by means of a magnetic coupling through a closed wall of the coupling housing 5 in that a first magnet element 6 is magnetically coupled within the coupling housing to a second magnet element 7 fastened outside the coupling housing 5 on a shaft end connected to the motor 3. The shaft 2 then has an interruption between the motor 3 and the further extension thereof in the coupling housing 5, and the corresponding wall of the coupling housing 5 is formed continuously and without an opening. The magnet elements 6, 7 are illustrated in a dashed manner in FIG. 1 as an alternative.

The driveshaft 2 is produced for example from litz wires, in particular in twisted or stranded form, or is formed as a helical spring or is formed in a combination of both variants by a core surrounded by a helical spring on the one hand so as to be able to transfer high rotational speeds in the region of a few thousand revolutions per minute and on the other hand so as to be flexible during this process.

In order to cool such a shaft during operation on the one hand and on the other hand so as to reduce the friction by lubrication, a cooling and lubricating liquid is usually provided within the channel 8 formed in the hollow catheter 1 and is advantageously biocompatible. The liquid is fed to the coupling housing 5 via an inflow channel 9 and is transported along the channel 8. For this purpose, the inflow channel 9 is connected to a first pump, which is formed in the exemplary embodiment as a diaphragm pump 10. Diaphragm pumps in this context have the property of being controllable in a very reliable and reproducible manner in order to be able to control generated pressures and flow rates in an exact manner. The use of magnetically actuated diaphragm pumps has proven to be particularly advantageous in this context. A magnet device 10a is therefore illustrated in FIG. 1, which serves as a drive for the diaphragm pump 10, wherein the magnet device 10a is actuated by an electric control device 11.

The diaphragm pump 10 sucks liquid from an inflow reservoir 12, as is illustrated by the arrow 13, and transports this at an adjustable flow rate and an adjustable pressure into the coupling housing 5 via the inflow channel 9. The liquid spreads in the coupling housing 5 and in particular moves in the direction of the arrow 14 along the channel 8 in the direction of the distal end 1b of the hollow catheter. The movement along the channel 8 can be assisted for example by the rotation of the shaft 2, when this has an at least partially helical outer contour and rotates in a suitable direction of rotation.

Although the rotation of the shaft 2 may assist the movement of the liquid along the channel 8, it is possible in some exemplary embodiments to determine the contribution of the rotation of the shaft to the delivery capacity so as to thus adapt the delivery capacity of the pump(s). In other words, the delivery capacity provided on account of the rotation of the shaft is compensated for by an adaptation of the delivery capacity of the pumps. The determination of the delivery capacity on the basis of the rotation of the shaft may then also be interpreted as a disturbance variable, which is compensated for by the adaptation of the delivery capacity of the pumps in order to ensure a predetermined delivery capacity through the channel. The delivery capacity of the shaft 8 may be dependent inter alia on the rotational speed of the shaft, possibly wear on the shaft, the deflection of the catheter, or the like. Although these variables can be determined, a compensation of the resultant delivery capacity of the shaft by the pump is often easier.

Flow rates in the range of microliters or millilitres per hour can usually be set by means of the actuation of the diaphragm pump 10.

In order to be able to suitably control or regulate corresponding flow rates and/or pressures, at least one suitable sensor 15 is provided in the channel 8 and is connected by means of a communication line 16 to the control device 11. The sensor 15 may be formed for example as a pressure sensor, as a flow rate sensor, or as a combined sensor for detecting the pressure and the flow rate.

In the shown exemplary embodiment the sensor 15 is assigned to the first diaphragm pump 10 and detects the pressure generated by this first pump and/or the corresponding flow rate.

In accordance with the exemplary embodiment of FIG. 1 the channel 8 is divided in the longitudinal direction into a first channel region 8a, through which liquid flows in the direction from the coupling housing 5 to the distal end 1b of the hollow catheter 1 in the direction of the arrow 14, and a second channel region 8b, which is formed as a return channel. The two channel regions 8a, 8b are thus connected in series and together form the channel 8.

Figure 3:
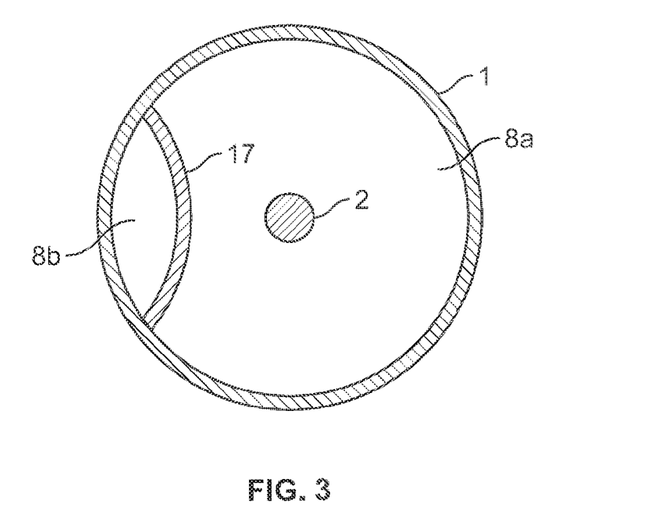
FIG. 3 shows a cross section through a hollow catheter.
Figure 4:
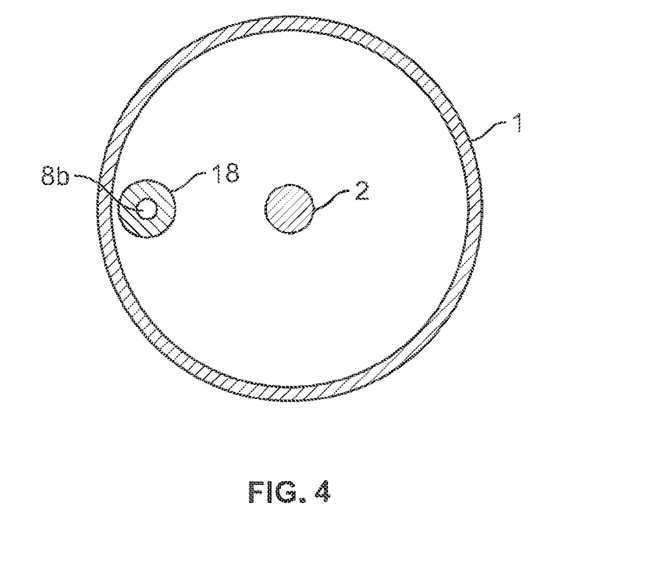
FIG. 4 shows a cross section through a further hollow catheter.

The return channel 8b may be separated from the first channel region 8a for example by a partition wall 17, which is illustrated in FIG. 3, or the second channel region/return channel 8b may be formed by a cannula 18, which extends within the hollow catheter 1. This variant is illustrated in FIG. 4 in cross section.

The return channel 8b is formed in accordance with FIG. 1 in such a way that it causes a return flow of the liquid into the coupling housing 5 and from there into a second diaphragm pump 19. The second diaphragm pump 19 may advantageously be formed as a magnetic diaphragm pump having a magnet device 19a which is actuated by the control device 11 and forms the drive of the diaphragm pump 19. The diaphragm pump 19 suctions the liquid from the return channel 8b and guides this via a discharge channel 20 into a discharge reservoir 21.

The control device 11 is additionally connected to a second sensor 22, which, similarly to the first sensor 15, can be formed as a flow path sensor and/or as a pressure sensor and is assigned to the return channel 8b and therefore to the second diaphragm pump 19. By way of example, the flow rate of the return channel 8b or the suction pressure of the second diaphragm pump 19 can be detected by the second sensor 22. The parameters detected by the second sensor 22 are fed via a second communication line 23 to the control device 11.

The control device 11 is in turn connected to an electric supply connection 11a, which supplies the control device with a low DC voltage (low voltage). The control device 11 generates pulses, which are fed to the magnet devices 10a, 19a in order to drive the first and second diaphragm pump 10, 19. The flow rates and/or pressures generated by the first and second diaphragm pump 10, 19 can be controlled by means of the frequency and the stroke of the pulses generated by the control device 11.

Figure 2:
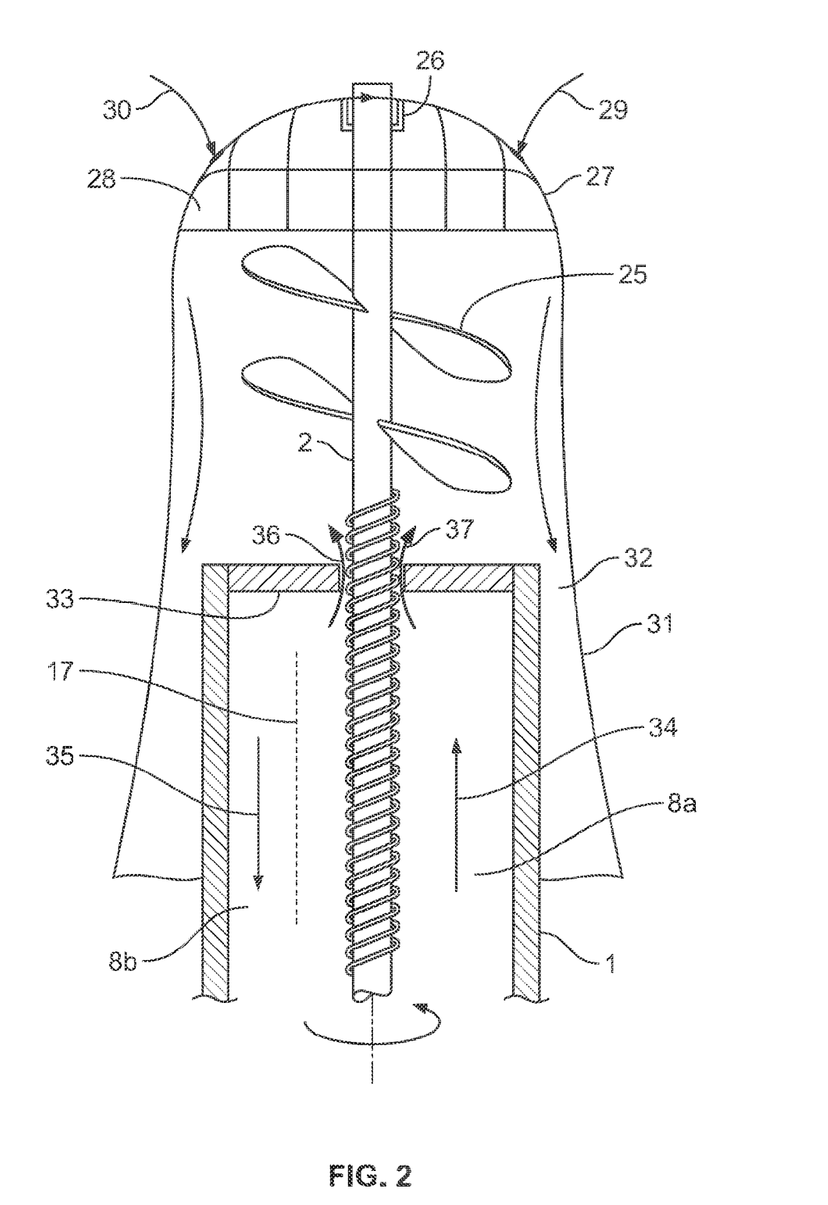
FIG. 2 shows the end of a hollow catheter in a longitudinal section with a distally fastened rotary pump for operation in a blood vessel.

FIG. 2, as an example for a use of a hollow catheter having a driveable shaft, shows an implantable blood pump 24, which is formed as a rotary pump having a rotor 25 with delivery elements. The rotor 25 is directly connected to the shaft 2, which is mounted in the housing 27 of the blood pump at the distal end of the rotor 25 in a rotary bearing 26. The blood pump 24 suctions blood via suction openings 28 at its distal end in the direction of the arrows 29, 30 and transports this externally past the hollow catheter 1 via an annular channel 32 formed by an outflow tube 31 into a blood vessel (not illustrated).

The shaft 2 is mounted at the end of the hollow catheter 1 in a bushing bearing 33, which on the one hand is to allow high rotational speeds, and on the other hand is to be as tight as possible in order to prevent or to limit a liquid exchange along the shaft 2. In particular, blood is to be prevented from passing from the interior of the housing 27 of the blood pump 24 into the hollow catheter 1, i.e. into the channel 8.

In FIG. 2 a partition wall 17 is illustrated in a dashed manner in order to indicate the separation between the first channel region 8a of the channel 8 and the second channel region/return channel 8b. The inflow of the liquid through the first channel region 8a in the direction of the arrow 34 to the distal end of the hollow catheter 1 and the return flow in the direction of the arrow 35 through the second region 8b of the channel 8 is thus made possible. The rotary shaft 2 can thus be supplied with the liquid along its entire length.

In order to prevent the inflow of blood into the channel 8, an overpressure of the liquid in the interior of the hollow catheter 1, i.e. in the channel 8, can be set, which causes liquid to flow at a very slow flow rate from the channel 8 into the housing of the blood pump 24, as indicated by the arrows 36, 37. By way of example, an outflow rate of a few microliters or millilitres per day can be set here, which represents a difference between the feed rate in the first channel region 8a and the return rate in the return channel 8b. This difference can be set and measured as the difference of the delivery rates between the first pump 10 and the second pump 19.

Figure 5:
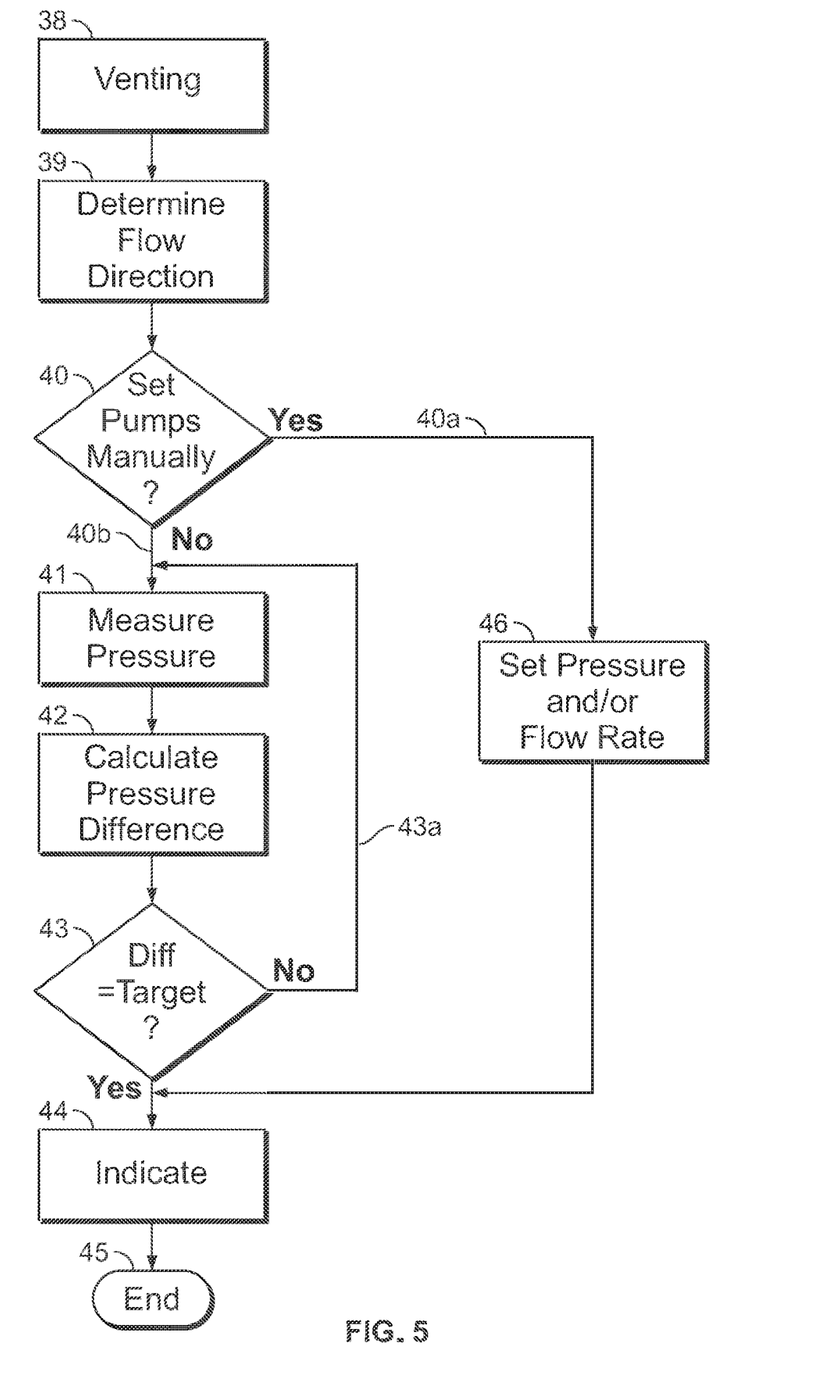
FIG. 5 shows a method sequence for a method for operating a supply device.

A flow diagram for a method for operating the shown supply device is illustrated in FIG. 5. In a first step 38 a venting of the channel 8 inclusive of the coupling housing 5 is performed in that liquid is fed by means of the first pump 10. Following the venting of the channel 8 and of the pumps, of which the speed is adjustable, the direction of movement (forwards/backwards) in which the liquid is to be moved through the channel 8 is determined in a second step 39. The diaphragm pumps 10, 19 and the reservoirs 12, 21 can allow both directions of movement of the liquid. The pressures generated by the diaphragm pumps 10, 19 are set depending on the direction of movement of the liquid.

In a third step 40 is it decided whether the capacities (performances) of the pumps are to be set manually. If the pumps are to be manually set, the rest of the process proceeds via the path 40a, and in a step 46 the pressures and/or flow rates of the two pumps are set. This variant is usually selected when the flushing rate, i.e. the flow rate through the channel 8, is to be small and constant.

If a manual actuation is to be selected, the continued path proceeds via the arrow 40b, and the automatic actuation of the pumps is started in a fourth step 41. For this purpose the pressure is firstly detected at the two pressure sensors 15, 22 in the step 41, a pressure difference is calculated from this, and from this the actuation of the pumps 10, 19 is calculated in a fifth step 42 by corresponding pulses of the control device 11. Here, the sought pressure difference may also be variable over time, for example varying periodically.

In a sixth step 43 the generated pressure difference is compared with the target pressure difference. If the actual pressure difference corresponds to the target pressure difference, the pressure difference or a flushing rate calculated herefrom for example is thus indicated in a seventh step 44 and the method is ended in an eighth step 45. The ending of the method means that the supply device is in a stable operating state and the pumps 10, 19 are actuated and operate accordingly. If it is determined in the sixth step 43 that the actual pressure difference does not correspond to the target pressure difference, the method jumps back via the path 43a to the fourth step 41, in which the pressure difference is measured, and from this the new actuation of the pumps is determined in a regulation step.

Instead of the pressure measurements and corresponding pressure regulation of the differential pressure, the flow rate may also be measured and a corresponding flow rate difference can be set as control variable.

Figure 6:
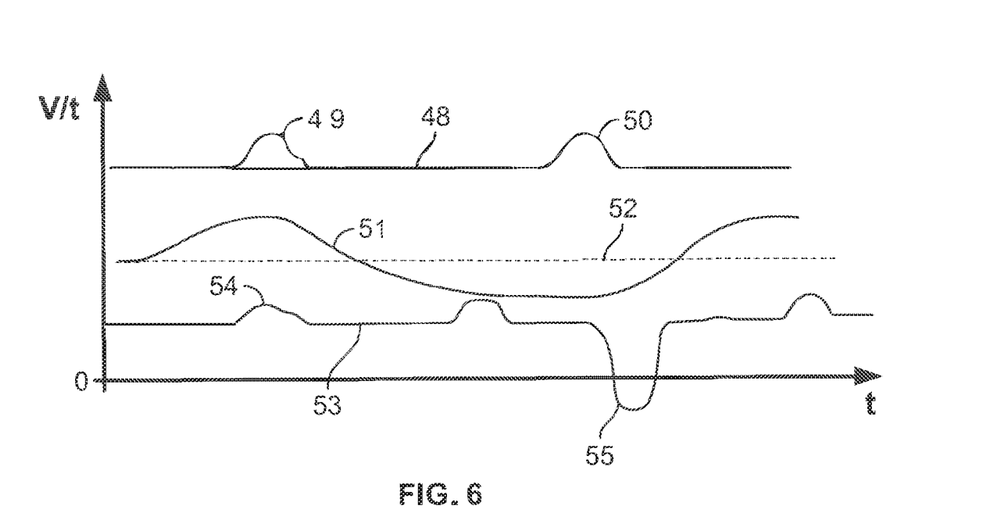
FIG. 6 shows a graph reproducing the course over time of flow rates in three different variants, and, FIG. 7 shows a graph reproducing the course over time of the liquid pressure.

A typical course over time of flow rates in three exemplary variants is shown in FIG. 6. The flow rate is indicated in volume per time on the y-axis of the graph, whereas the time is plotted on the x-axis. A first curve 48 by way of example shows the flow rate, measured by the sensor 15 or the sensor 22, wherein the flow rate is constant over a large portion of the time, but the flow rate is changed from time to time, for example every twenty seconds or in each case after a few minutes, by a temporary increase 49, 50 of the flow rate. There is thus no stationary flow formed in the channel 8, which might leave certain regions of the channel untouched as what are known as deadwater regions, such that liquid located there does not move on further. A change to the flow rate generates turbulence and non-stationary flow conditions, which then also determine the deadwater areas and exchange the liquid there.

A further object of a corresponding control of the flow rate is to prevent particles located in the liquid and which for example are created by abrasion of the rotating shaft 2 from being moved on further where possible, such that these do not exit through the bearing 33, illustrated in FIG. 2, in the region of the blood pump and cannot enter into the body of a patient.

If the flow rates detected by the two sensors 15, 22 are plotted in the same graph, an increased flow rate with a particularly noticeable difference of the flow rates can be set for example particularly in the regions 49, 50, which indicates that some of the liquid in these regions 49, 50 exits intermittently in very small quantities from the channel 8 and passes into the interior of the pump housing of the blood pump and thus flushes away any quantities of the blood deposited there from the bearing 33.

In a second variant 51 of the course of the flow rate, this is varied periodically around a constant course 52, for example in the form of a sine curve. A constantly changing flow with flow conditions that likewise change constantly and guarantee a liquid exchange in all regions of the channel 8 is thus provided.

In the third variant, which is illustrated in the curve 53, apart from temporary periodic increases 54 of the flow rate, the flow direction is also reversed, shown on the basis of the example of the reduction 55 of the flow rate. The reversal of the flow causes a change to the flow direction of the liquid in the channel 8 and therefore likewise the exchange of liquid in deadwater areas. Such a reversal of the flow direction can occur for example at intervals from five to ten minutes.

Figure 7:
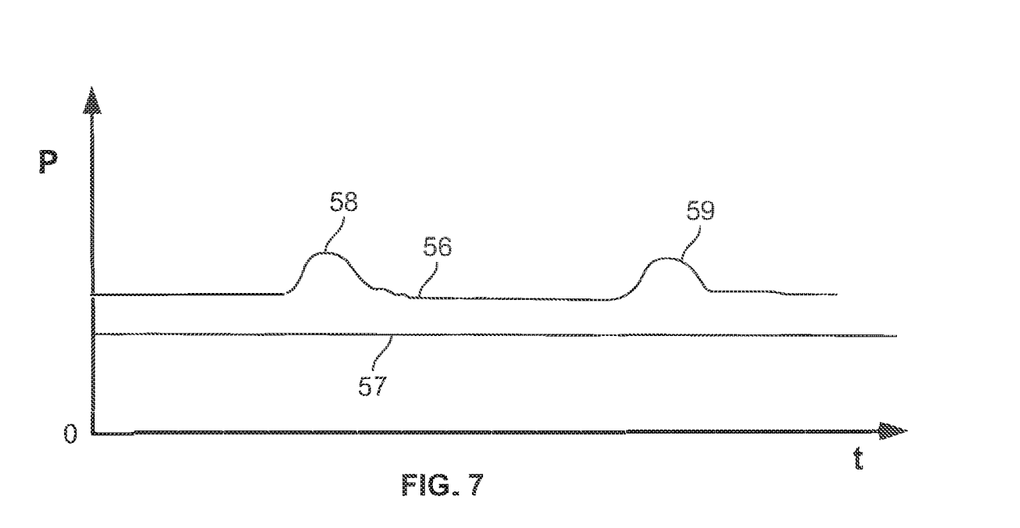

In FIG. 7 measured pressure values are plotted on the y-axis over time t, wherein a first curve 56 indicates the pressure in the region of the sensor 15 and a second curve 57 indicates the pressure in the region of the sensor 22. It can be seen that in two regions 58, 59 the pressure is temporarily increased by the first diaphragm pump 10, whereas the pressure in the region of the return line, detected by the sensor 22, remains constant. This causes liquid to flow off into the pump housing through the bearing 33 in the regions of the increased pressure 58, 59, thus relieving the pressure in the channel 8.

As a result of the above-described invention, a supply device in the form of a flushing device for a hollow catheter for a blood pump is provided, in which few wear parts are used and therefore stable operation with low liquid losses thus can be ensured over a long period of time.

The invention claimed is:

1. A hollow catheter comprising:
   a channel comprising;
   an inflow channel region and an outflow channel region fluidly connected in series;
   a supply device for supplying the channel with a liquid, wherein the supply device comprises:
      a diaphragm pump; and
      a control device, which controls the diaphragm pump in respect of a generated pressure or a delivery rate to prevent blood from entering the channel;
   wherein a sensor is assigned to the diaphragm pump, said sensor being a liquid pressure sensor, an electric sensor for detecting a power consumption of the diaphragm pump, or a flow rate sensor.

2. The hollow catheter of claim 1, comprising one or more further diaphragm pumps, wherein:
   the diaphragm pump and the one or more further diaphragm pumps are arranged at points of the channel distanced from one another;
   the control device is configured to control each of the diaphragm pump and the one or more further diaphragm pumps individually in respect of the generated pressure and/or the delivery rate;
   a sensor is assigned to each of the one or more further diaphragm pumps;
   wherein, each of the sensors is assigned to the one or more further diaphragm pumps is one of a liquid pressure sensor, an electric sensor for detecting a power consumption of the one or more diaphragm pumps, and a flow rate sensor.

3. The hollow catheter of claim 1, wherein a catheter pump comprises the hollow catheter.

4. The hollow catheter of claim 3, wherein the catheter pump is configured for intraventricular operation within a heart.

5. A method for operating a supply device that supplies a channel of a hollow catheter with an inflow channel region and an outflow channel region fluidly connected in series with a liquid, the supply device having at least one diaphragm pump with a sensor assigned thereto, the method comprising:
   using the sensor, detecting an operating parameter of the at least one diaphragm pump, the operating parameter being one or more of liquid pressure at one or more points in the channel, power consumption of the at least one diaphragm pump, or flow rate;
   calculating a generated pressure or delivery rate based on the operating parameter detected by the sensor to prevent blood from entering the channel; and
   controlling the at least one diaphragm pump according to the generated pressure and/or delivery rate.

6. A method for operating a supply device that supplies a channel of a hollow catheter with an inflow channel region and an outflow channel region fluidly connected in series with a liquid and has at least two diaphragm pumps, arranged at points of the channel distanced from one another, the method comprising:
   detecting a value of an operating parameter for each of the diaphragm pumps, the operating parameter being one or more of liquid pressure at one or more points in the channel, power consumption, or flow rate; and controlling the parameter value of at least one operating parameter for each of the diaphragm pumps in a coordinated manner to prevent blood from entering the channel.

7. The method of claim 6, wherein the controlled parameter values of the diaphragm pumps lie at a ratio to one another that is dependent in a predetermined manner on the detected values of the liquid pressure in the channel.

8. The method of claim 6, wherein the controlled parameter values of the diaphragm pumps are variable over time in accordance with a fixed schema.

9. The method of claim 6, wherein the controlled parameter values of the diaphragm pumps are changed periodically over time following a start-up phase.

10. The method according to claim 6, wherein the controlled operating parameters of the diaphragm pumps are respective values of the liquid pressure generated by the diaphragm pumps, respective delivery capacities of the diaphragm pumps, or respective flow rates of the diaphragm pumps.

11. The method according to claim 6, comprising setting a fixed pressure difference between the diaphragm pumps.

12. The method according to claim 6, comprising setting a fixed flow rate difference between the diaphragm pumps.

13. The method according to claim 12, wherein setting a fixed flow rate difference between the diaphragm pumps comprises setting a fixed flow rate difference of less than 100 millilitres per day, less than 10 millilitres per day, or less than 1 millilitre per day.

14. The method according to claim 6, comprising:
controlling the diaphragm pumps to reverse a direction of movement of the liquid.

* * * * *

UNITED STATES PATENT AND TRADEMARK OFFICE
CERTIFICATE OF CORRECTION

PATENT NO. : 10,780,205 B2
APPLICATION NO. : 16/228005
DATED : September 22, 2020
INVENTOR(S) : Tiller et al.

Page 1 of 1

It is certified that error appears in the above-identified patent and that said Letters Patent is hereby corrected as shown below:

In the Specification

Column 1, Line 18 - After "pump", insert --.--.

Column 6, Line 60 - Delete "8" and insert --2-- therefor.

In the Claims

Column 10, Line 32 - In Claim 2, after "sensors", delete "is".

Column 10, Line 35 - In Claim 2, after "more", insert --further--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*